United States Patent
Tano et al.

(10) Patent No.: US 8,265,764 B2
(45) Date of Patent: Sep. 11, 2012

(54) ARTIFICIAL VISION SYSTEM

(75) Inventors: Yasuo Tano, Kobe (JP); Takashi Fujikado, Toyonaka (JP); Yutaka Fukuda, Toyonaka (JP); Tetsuya Yagi, Toyonaka (JP)

(73) Assignees: Nidek Co., Ltd., Gamagori-Shi (JP); Yasuo Tano, Kobe-Shi (JP)

( * ) Notice: Subject to any disclaimer, the term of this patent is extended or adjusted under 35 U.S.C. 154(b) by 679 days.

(21) Appl. No.: 10/537,266

(22) PCT Filed: Dec. 4, 2003

(86) PCT No.: PCT/JP03/15566
§ 371 (c)(1),
(2), (4) Date: Jun. 1, 2005

(87) PCT Pub. No.: WO2004/049986
PCT Pub. Date: Jun. 17, 2004

(65) Prior Publication Data
US 2006/0058857 A1  Mar. 16, 2006

(30) Foreign Application Priority Data
Dec. 5, 2002  (JP) ................. 2002-354330

(51) Int. Cl.
*A61N 1/00* (2006.01)
*A61B 5/04* (2006.01)
(52) U.S. Cl. ............. 607/54; 607/53; 607/141; 600/383
(58) Field of Classification Search ............. 607/53–54, 607/141; 600/383
See application file for complete search history.

(56) References Cited

U.S. PATENT DOCUMENTS

| | | | |
|---|---|---|---|
| 3,449,768 A | 6/1969 | Doyle | |
| 4,271,841 A * | 6/1981 | Friedman | 607/53 |
| 4,969,468 A * | 11/1990 | Byers et al. | 600/373 |
| 5,109,844 A * | 5/1992 | de Juan et al. | 607/53 |
| 5,496,355 A * | 3/1996 | Lipsky | 607/53 |
| 5,556,423 A * | 9/1996 | Chow et al. | 623/6.63 |
| 5,674,263 A | 10/1997 | Yamamoto et al. | |
| 5,782,894 A * | 7/1998 | Israel | 607/53 |
| 5,935,155 A | 8/1999 | Humayun et al. | |
| 6,347,250 B1 * | 2/2002 | Nisch et al. | 607/54 |
| 6,720,497 B1 * | 4/2004 | Barsne | 174/102 R |
| 6,792,314 B2 * | 9/2004 | Byers et al. | 607/53 |
| 2003/0097166 A1 * | 5/2003 | Krulevitch et al. | 607/116 |
| 2003/0158588 A1 * | 8/2003 | Rizzo et al. | 607/54 |
| 2004/0078064 A1 * | 4/2004 | Suzuki | 607/54 |
| 2004/0102843 A1 * | 5/2004 | Yagi | 623/4.1 |

(Continued)

FOREIGN PATENT DOCUMENTS
EP     325201 A2 *  7/1989
(Continued)

*Primary Examiner* — Nicole F Lavert
(74) *Attorney, Agent, or Firm* — Oliff & Berridge, PLC

(57) ABSTRACT

An object is to provide an artificial vision system ensuring a wide field of view without damaging a retina. In the artificial vision system, a plurality of electrodes (23) are to be implanted so as to stick in an optic papilla of an eye of a patient. A signal for stimulation pulse is generated based on an image captured by an image pick up device (11) to be disposed outside a body of the patient. The electrical stimulation signals outputted from the electrodes (23) based on the signals for stimulation pulse stimulate an optic nerve of the eye, thereby enabling the patient to visually recognize the image from the image pickup device (11).

1 Claim, 4 Drawing Sheets

U.S. PATENT DOCUMENTS

| | | |
|---|---|---|
| 2005/0004625 A1* | 1/2005 | Chow .............................. 607/54 |
| 2005/0090875 A1* | 4/2005 | Palanker et al. ................ 607/54 |

FOREIGN PATENT DOCUMENTS

| | | |
|---|---|---|
| JP | A 53-105089 | 9/1978 |
| JP | A 53-123588 | 10/1978 |
| WO | WO 94/26209 | 11/1994 |
| WO | WO 96/39221 | 12/1996 |
| WO | WO 01/74444 A1 | 10/2001 |
| WO | WO 02/40095 A1 | 5/2002 |
| WO | WO 02/064072 A1 | 8/2002 |
| WO | WO 02/080828 A1 | 10/2002 |

* cited by examiner (a)

(b)

(a)

(b)

WAVEFORM OF DIGITAL VALUE 0

WAVEFORM OF DIGITAL VALUE 1

ARTIFICIAL VISION SYSTEM

TECHNICAL FIELD

The present invention relates to an artificial vision system for artificially giving a visual signal, and more particularly to an artificial vision system of an optic papilla stimulating type for applying an electrical signal to an optic papilla in which nerve fibers running throughout a retina join, thereby inducing restoration of vision.

BACKGROUND ART

Retinitis pigmentosa, age-related macular degeneration, and others cause visual defects and may lead to blindness at an advanced stage. Human eyes normally work such that, when light is irradiated to a retina, a light signal is converted to an electrical signal through photoreceptor cells, and this electrical signal is turned into a pulse signal through retinal ganglion cells and is transmitted to a brain. When the retinitis pigmentosa, age-related macular degeneration, and others occur, the photoreceptor cells are reduced or deadened and thus could not convert the light signal to the electrical signal. Consequently, a person would lose his vision.

In recent years, various attempts have been proposed to recover the vision of patients with vision loss from the above causes.

For example, Japanese Patent No. 3514464 discloses an invention related to an artificial vision system utilizing a retina stimulating type implant. This system is arranged such that a microphotodiode having a sensitivity to visible and infrared light is implanted under a retina to receive light of a picture image that has been amplified and modulated by a NeuronNet computer via a CCD camera, thereby providing vision.

Regarding the artificial vision system, on the other hand, an optic papilla stimulating type implant for electrically stimulating an optic nerve from surrounding portions and a brain cortex stimulating type implant for electrically stimulating a visual cortex have also been studied as well as the above retina stimulating type implant.

In the retina stimulating type implant disclosed in Japanese Patent No. 3514464 however, the microphotodiode is generally located on only a part of the retina, resulting in a problem that a visual field is extremely narrow (about 10° of a visual angle).The patient therefore could not easily distinguish the surrounding circumstances and particularly would find it difficult to visually recognize a moving object. To ensure a wide visual field, on the contrary, the microphotodiode has to be implanted in a wider area. However, the implanting operation onto a spherical retina would be hard. In the case of the retina stimulating type implant, the retina is peeled for implantation of electrodes. This would cause a problem that portions surrounding the electrode setting site are also peeled, which leads to retinal detachment after the operation.

On the other hand, the optic papilla stimulating type implant for electrically stimulating the optic nerve from the surrounding portions has a disadvantage that the number of electrodes could not be increased and therefore effective vision could not be provided. The brain cortex stimulating type implant has also a problem that an information processing system is complicated and it is hard to give stimulation close to an ordinary view.

To solve the above problems, the present invention has an object to provide an artificial vision system of an optic papilla stimulating type which is a new technique for restoring vision, capable of ensuring a wide visual field without damaging a retina.

DISCLOSURE OF INVENTION

An artificial vision system of the present invention made to achieve the above object is characterized in that a plurality of electrodes are to be implanted so as to stick in an optic papilla of an eye of a patient, a signal for stimulation pulse is generated based on an image captured by an image pickup device to be disposed outside a body of the patient, the electrodes output an electric stimulation signal based on the generated signal for stimulation pulse to stimulate an optic nerve of the eye, thereby enabling the patient to recognize the image from the image pickup device.

In the artificial vision system of the present invention, preferably, the plurality of electrodes are to be implanted so as to individually stick in the optic papilla.

According to the present invention, the electrodes are to be implanted so as to stick in the optic papilla in which nerve fibers for transmitting the pulse signal of retinal ganglion cells join (converge), in order to directly stimulate the optic nerve consisting of a bundle of the nerve fibers. It is therefore possible to deal with image information on a range of an object space that a person can inherently visually recognize from the light received at a retina. To this end, a patient can visually recognize the object space captured by a photographing (imaging) device and thus a wide visual field is ensured. The electrodes, which are to be located on the optic papilla, cause no damage to the retina and have no possibility of causing retinal detachment.

Furthermore, the artificial vision system of the present invention is characterized in further comprising: an external device which is to be disposed outside the body and performs predetermined optimizing processing the image captured by the image pickup device to generate the signal for stimulation pulse; and an internal device which is to be implanted in the body and converts the signal for stimulation pulse into the electrical stimulation signal to output the electrical stimulation signal from the electrodes.

In the artificial vision system of the present invention, preferably, the external device includes the image pickup device, an image processing device which performs the predetermined optimizing processing to generate the signal for stimulation pulse, and a power supply.

Furthermore, in the artificial vision system of the present invention, preferably, the image processing device adjusts parameters of the electrical stimulation signal to be outputted from the electrodes.

The artificial vision system is constructed of the separately provided external device and internal device as above. Accordingly, the external device can be provided with many functions and an increased capacity of the power supply, which allows stable long-term use.

In the artificial vision system of the present invention, preferably, the signal for stimulation pulse and power are transmitted from the external device to the internal device by electromagnetic induction occurring between a primary coil which is to be attached to a skin of the body and a secondary coil which is to be implanted in advance in the body.

BEST MODE FOR CARRYING OUT THE INVENTION

Figure 1:
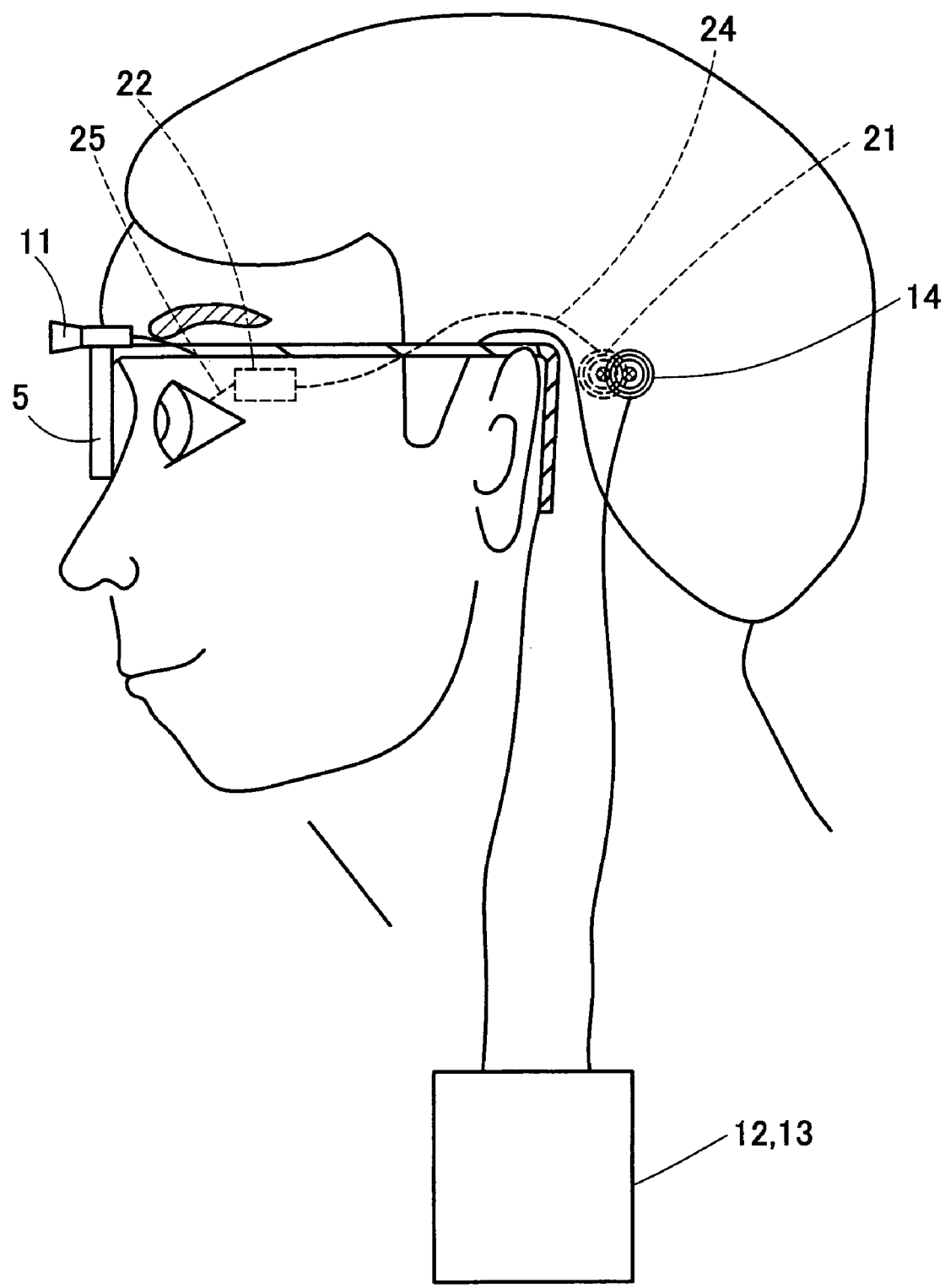
FIG. 1 is a view showing an in-use state of an artificial vision system in an embodiment.
Figure 2:
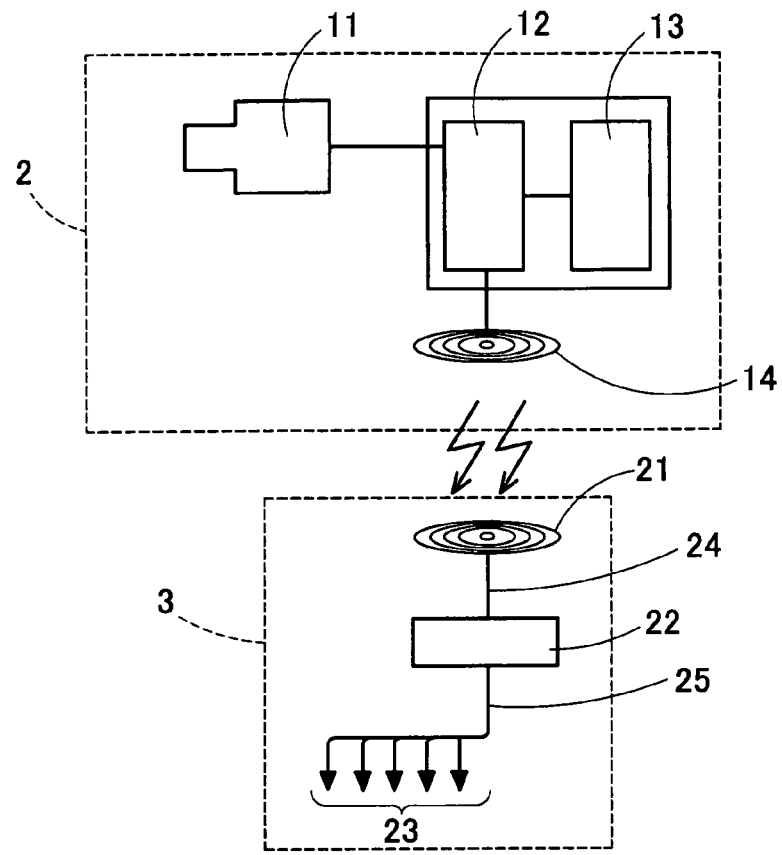
FIG. 2 is a block diagram showing a schematic structure of the artificial vision system in the embodiment.

A detailed description of a preferred embodiment of an artificial vision system embodying the present invention will now be given referring to the accompanying drawings. FIG. 1 is a view showing an in-use state of the artificial vision system in the present embodiment. FIG. 2 is a block diagram showing a schematic structure of the artificial vision system.

The artificial vision system 1 in the present embodiment is constructed of an external device 2 which a patient wears in use and an internal device 3 which is surgically implanted in advance in the patient himself. The external device 2 is arranged such that a camera 11 is mounted on a visor 5 which the patient puts on like glasses to capture a video image of an object space in front of the patient who turns his face. For example, a CCD camera with an image pickup device of tens of thousands of pixels is used as the camera.

Figure 3:
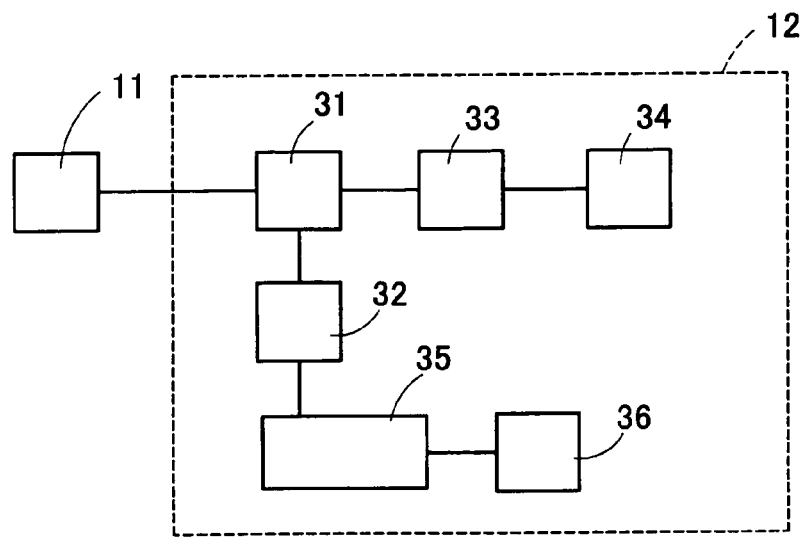
FIG. 3 is a block diagram showing an image processing device.

The camera 11 is connected to an image processing device 12 which conducts predetermined optimizing processing based on image data of the captured image and generates a signal for stimulation pulse for stimulating an optic nerve to provide vision. Herein, FIG. 3 is a block diagram showing the image processing device 12. The image processing device 12 includes an A/D converter 31 connected to the camera 11 and an imaging circuit 32 for converting the imaging signal read from the camera 11 into digital image data. The A/D converter 31 is connected to an image processing section 33 and further a buffer memory 34 which temporarily stores the image data image-processed in the image processing section 33.

The image processing section 33 is constructed of an image processing CPU (a microprocessor) and a memory storing a control program thereof and arranged to optimize the image data captured by the camera 11 and then generate the signal for stimulation pulse for stimulating the optic nerve.

The image processing device 12 includes a system controller 35 constructed of a control CPU (a microprocessor) and a memory storing a control program thereof. The system controller 35 is arranged such that parameters of the stimulation pulse (frequency, amplitude (electric current amount), lighting time length, and others) to be outputted from electrodes 23 can be adjusted by operation of an adjustment dial provided in an input operating part 36. In particular, there are separately provided a dial for adjusting brightness and contrast of an image to be visually recognized and a dial for adjusting parameters for electrical stimulation.

The imaging circuit 32 constituting the image processing device 12 is controlled from the system controller 35 to perform read processing of the imaging signal from the camera 11 and ON/OFF control of power supply to the camera 11.

Returning to FIG. 2, the external device 2 is provided with a power supply 13 for supplying power to the image processing device 12 and the internal device 3. This power supply 13 and the image processing device 12 are integrally formed in a compact size to be portable in a pocket of a patient's jacket or the like.

In the artificial vision system 1 in the present embodiment, electromagnetic induction occurring between coils is utilized to transmit the processed image data and power from the external device 2 to the internal device 3. Accordingly, in the external device 2, a primary coil 14 is connected to the image processing device 12. The internal device 3 is also provided with a secondary coil 21 in correspondence with the primary coil 14.

In the internal device 3, as shown in FIG. 2, the secondary coil 21 is connected to a receiving device 22 which receives the signal for stimulation pulse and power transmitted from the image processing device 12. A plurality of electrodes 23 each having a needle-shaped end are connected to this receiving device 22 through individually corresponding signal wires 25. The receiving device 22 includes a receiving section which receives the signal for stimulation pulse and the power and a signal processing section which converts the received signal for stimulation pulse into an electrical stimulation signal to be outputted from the electrodes 23.

The above internal device 3 is implanted in advance in the patient's body in a surgical operation. For instance, the secondary coil 21 and the receiving device 22 including signal wires 24 are implanted in a portion of the patient's head between the skin and the head bone as shown in FIG. 1. Especially, the secondary coil 21 is implanted in a portion hidden by his hairs so as to be inconspicuous when the primary coil is attached. The receiving device 22 is implanted near the eye to shorten the distance from the electrodes 23. These secondary coil 21, receiving device 22, and signal wires 24 are covered with an insulating material with high biocompatibility, such as polyimide.

Figure 4:
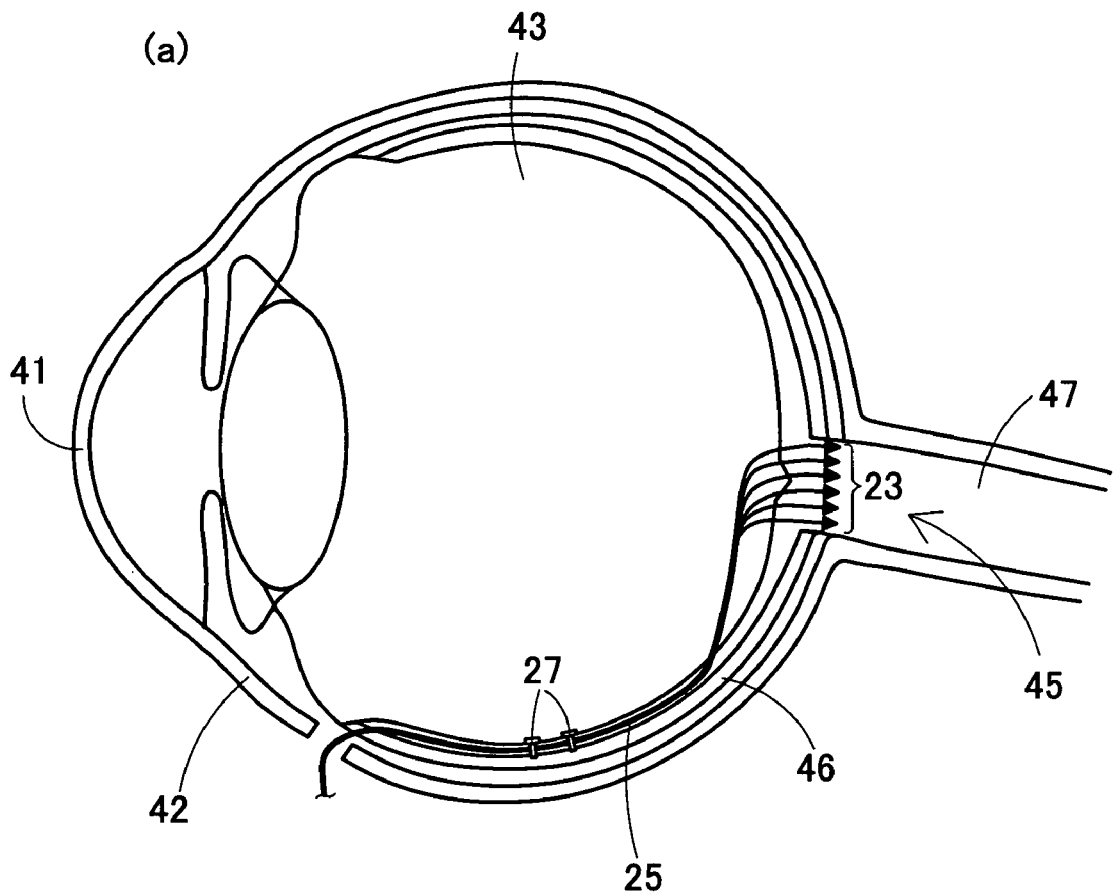
FIG. 4 is a sectional view of an eyeball, showing an implanted place of electrodes.
Figure 4:
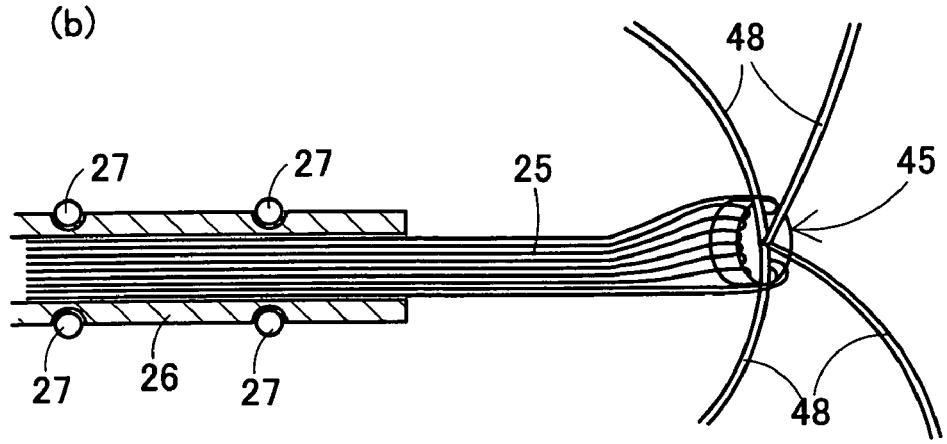

On the other hand, the electrodes 23 are implanted to directly stick in the optic papilla in which the nerve fibers for transmitting the pulse signal of the retinal ganglion cells join (converge). FIG. 4 is a view schematically showing an implanted state of those electrodes 23; FIG. 4(a) is a horizontal sectional view of a whole eyeball and FIG. 4(b) is a view showing the optic papilla. The signal wires 25 connecting the receiving device 22 to the electrodes 23 are inserted from a hole formed in a cornea (a black portion of the eye) 41 and sclera (a white portion of the eye) 42 forming an outer membrane of the eyeball and passes around a vitreous body 43 which has been replaced with an intraocular irrigating solution. To shorten the distance to the optic papilla 45, the signal wires 25 are inserted from the nose side (a lower side in the figure) into the eye. The signal wires 25 including the electrodes 23 attached to respective ends are individually coated with an insulating material with high biocompatibility, such as polyimide. The signal wires 25 are bundled up by a tube 26 and fixed with tacks 27 in the eye.

Meanwhile, light having entered in the eye through the cornea 41 reaches a retina 46 and is converted into an electrical signal through photoreceptor cells. This electrical signal is turned into a pulse signal through the retinal ganglion cells and sent to the cerebrum. From the retinal ganglion cells to the cerebrum, the nerve fibers running throughout the retina 46 join in the optic papilla 45 and exit the eyeball, forming an optic nerve 47 which is connected to the cerebrum. In the conventional artificial vision system, a microphotodiode is implanted underneath the retina 46 instead of the optic nerve and part of light having entered through the cornea 41 is converted into an electrical signal.

In the conventional artificial vision system, consequently, only the light having reached the microphotodiode, of the light having entered through the cornea 41, could be converted into an electrical signal. Thus, the system could ensure visual recognition of an object space in only an extreme narrow visual field. In the present embodiment, on the other hand, attention is given to the optic papilla 45 in which the nerve fibers running throughout the retina 46 join. Thus, the electrodes 23 are stuck into the optic papilla 45 to stimulate the optic nerve, ensuring a wide visual field. It is to be noted that not only the nerve fibers but also blood vessels 48 run through the optic papilla 45 as shown in FIG. 4(*b*), so that the electrodes 23 are implanted so as to stick in the optic papilla 45 while avoiding the nerve fibers and blood vessels 48.

The following explanation is made on the operation of the artificial vision system 1 in the present embodiment. The internal device 3 is implanted in advance in the patient in the surgical operation. The artificial vision system 1 is ready for use when the patient puts on the external device 2. Specifically, the patient wears the visor 5 of the internal device 3 like glasses and carries the integrally formed image processing device 12 and power supply 13 in a pocket of his jacket. Furthermore, the primary coil 14 attachable with an adhesive seal is adhered on the skin corresponding to the position where the secondary coil 21 has been implanted.

Then, upon turn on of the power supply, the camera 11 captures an image in front of the patient who turns his head and sends the image data to the image processing device 12. The image processing device 12 optimizes the captured image data and generates and modulates a signal for stimulation pulse for stimulating the optic nerve. To be more specific, in the image processing device 12, the system controller 35 controls such that the imaging circuit 32 reads the imaging signal of the video image captured by the camera 11 and the A/D converter 31 converts the imaging signal into the digital image data.

The digital image data is optimized in accordance with the control program of the image processing section 33. The image data optimized in the image processing section 33 is temporarily stored in the buffer memory 34. The image processing section 33 further generates the signal for stimulation pulse for stimulating the optic nerve.

Power from the power supply 13 is sent along with the signal for stimulation pulse for stimulating the optic nerve into the internal device 3 owing to electromagnetic induction occurring between the primary coil 14 and the secondary coil 21. It is to be noted that the signal for stimulation pulse and the power may be sent in a time-sharing manner. The signal for stimulation pulse is transmitted to the receiving device 22 through the secondary coil 21. In the receiving device 22, the receiving section receives the signal for stimulation pulse along with the power and the signal processing section converts the signal for stimulation pulse into the electrical stimulation signal to be outputted from the electrodes 23.

Figure 5:
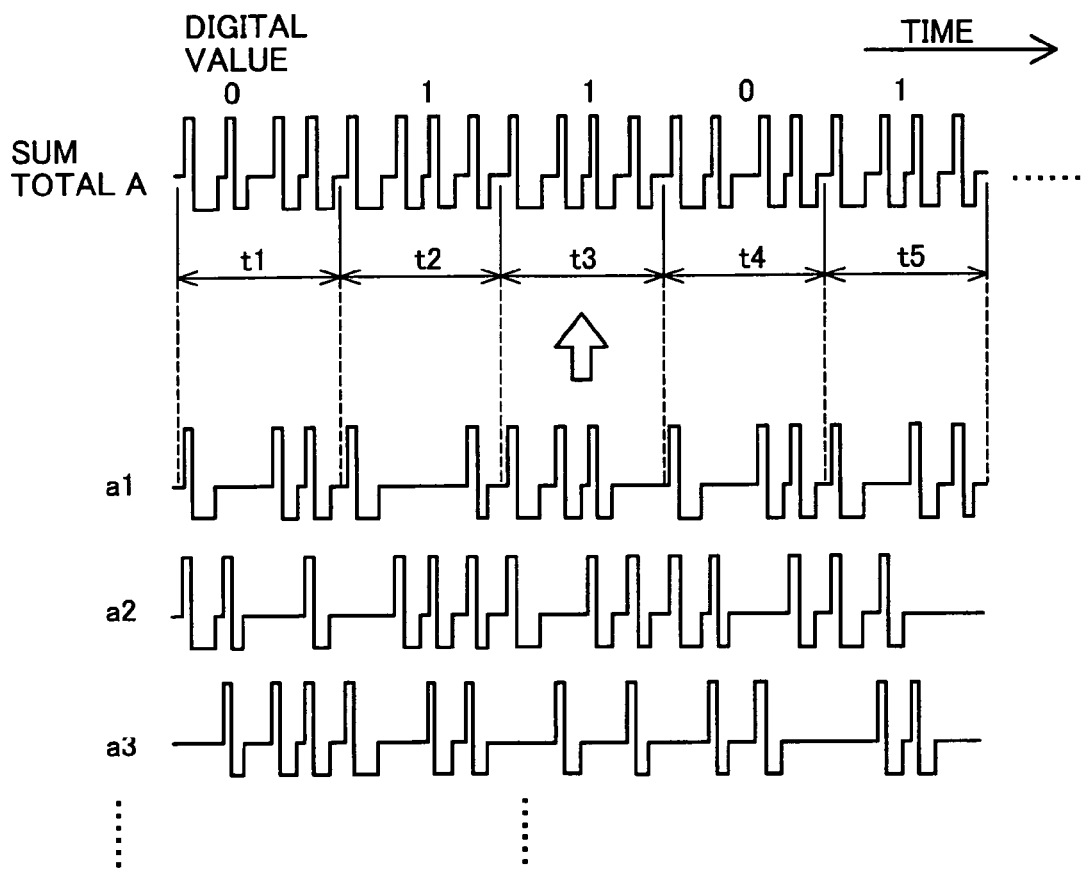
FIG. 5 is a view showing an example of an electrical stimulation signal outputted from the electrodes.
Figure 5:
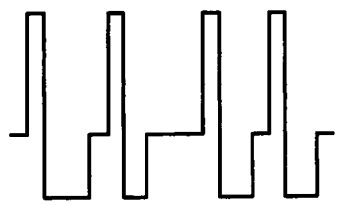
Figure 5:
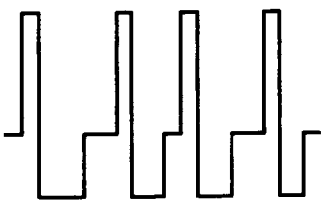

Herein, FIG. 5 is a view showing an example of the electrical stimulation signals to be outputted from the electrodes 23. As shown in FIG. 5(*a*), the sum total A of the electrical stimulation signals to be outputted from the electrodes 23 (the sum total A is shown in a state where the signals are standardized by the pulse and adjusted to have the same height) consists of a combination of two waveform patterns. These two waveform patterns are different in waveform per unit of time "t" as shown in FIG. 5(*b*) (the unit of time is determined as a stimulation signal time length of one stimulation needed for restoring vision); one waveform pattern represents a digital value "0" and the other represents a digital value "1". In the case where the electrical stimulation signal is outputted, used is the sum total of the electrical stimulation signals, i.e., the electrical stimulation signal consisting of a combination of the two waveform patterns of the stimulation signals, thus restoring vision and also representing a combination of digital values "0" and "1" as transmission data. It should be understood that this electrical stimulation signal is merely an example and not limited thereto. Any signal may be adopted if only it can induce the restoration of vision.

The electrical stimulation signal outputted from the electrodes 23 passing through the optic papilla 45 in which the electrodes 23 are stuck and the optic nerve 47 to stimulate the cerebrum, thereby enabling the patient to visually recognize the object space captured by the camera 11. In the present embodiment, the electrical stimulation signal is applied to the optic papilla 45 in which the nerve fibers running throughout the retina 46 join, which enables the patient to recognize the image information in a range of the object space that a person can inherently visually recognize from the light received at the retina 46. Consequently, the patient can visually recognize in a wide visual field.

The artificial vision system 1 with the electrodes 23 to be implanted so as to stick in the optic papilla 45 can prevent damage to the retina which would be caused by the conventional retina stimulating type implant, and hence has no problem causing retinal detachment. An implanting manner of the electrodes 23 in the optic papilla 45 can be established based on the radial optic neurotomy having been established for central retinal vein occlusion.

Since the system 1 is constructed of the external device 2 and the internal device 3, the external device 2 can be provided with many functions. In the present embodiment, for example, parameters of the stimulation pulse emitted from the electrodes 23 can be adjusted by operation of the adjustment dial provided in the input operating part 36.

The above explanation is made on one embodiment of the artificial vision system and the present invention is not limited thereto and may be embodied in other specific forms without departing from the essential characteristics thereof.

Industrial Applicability

According to the present invention, as seen in the above explanation, a plurality of electrodes are to be implanted so as to stick in the optic papilla of the patient's eye, and the signal for stimulation pulse for stimulating the optic nerve is generated based on image data captured by an image pickup device to be disposed outside a patient's body, the electrodes output the electrical stimulation signal based on the generated signal for stimulation pulse to stimulate the optic nerve. Accordingly, there can be provided an artificial vision system of an optic papilla stimulating type as a new technique for restoration of vision and capable of ensuring a wide visual field without damaging a retina.

The invention claimed is:

1. An artificial vision system comprising:
   an external device adapted to be disposed outside a body of a patient, the external device including:
      an image pickup device configured to capture an image in front of the patient; and
      an image processing device configured to generate a signal for stimulation pulse by processing the image captured by the image pickup device; and
   an internal device adapted to be implanted in the body, the internal device including:
      a receiving device configured to receive the signal for stimulation pulse and configured to convert the signal for stimulation pulse into an electrical stimulation pulse signal;
      a plurality of electrodes each of which is configured to output the electrical stimulation pulse signal, has a needle-shaped end and sticks in an optic papilla of an eye before a bundle of nerve fibers exit the eye to form an optic nerve, each electrode having a predetermined length for placing its end in the optic nerve of the eye when the electrode is stuck in the optic papilla; and a plurality of signal wires which individually connects each electrode and the receiving device, the signal wires each being covered with an insulating material with high biocompatibility and having a length enough to reach each electrode stuck in the optic papilla from outside to inside of the eye; and a tube configured to bundle the plurality of signal wires together into one, wherein the electrodes, after being stuck in the optic papilla, output the electric stimulation pulse signal based on the signal for stimulation pulse which is generated based on the image captured by the image pickup device to stimulate the optic nerve, thereby enabling the patient to recognize the image captured by the image pickup device, and the electrodes are placed along a circumference of the bundle of nerve fibers.

* * * * *